United States Patent [19]

Kleeberg et al.

[11] 3,957,512

[45] May 18, 1976

[54] METHOD FOR THE PREPARATION OF RELIEF STRUCTURES

[75] Inventors: Wolfgang Kleeberg, Erlangen; Roland Rubner, Rottenbach; Wieland Bartel, Furth, all of Germany

[73] Assignee: Siemens Aktiengesellschaft, Munich, Germany

[22] Filed: Feb. 21, 1974

[21] Appl. No.: 444,552

[30] Foreign Application Priority Data

Feb. 22, 1973 Germany............................ 2308830

[52] U.S. Cl. .............................. 96/35.1; 96/115 R; 260/468 J; 260/47 CZ
[51] Int. Cl.² ...................... G03C 1/68; G03C 5/00
[58] Field of Search .............. 96/35.1, 115 R, 115 P

[56] References Cited
UNITED STATES PATENTS

| | | | |
|---|---|---|---|
| 3,475,176 | 10/1969 | Rauner............................ | 96/115 R |
| 3,650,746 | 3/1972 | Builey................................ | 96/35.1 |
| 3,753,720 | 8/1973 | Kloczewski et al.................. | 96/35.1 |
| 3,801,638 | 4/1974 | Cerwonka........................ | 96/115 P |
| 3,847,767 | 11/1974 | Kloczewski........................ | 96/115 P |
| 3,858,510 | 1/1975 | Kai et al............................. | 96/115 P |

*Primary Examiner*—Jack P. Brammer
*Attorney, Agent, or Firm*—Kenyon & Kenyon Reilly Carr & Chapin

[57] ABSTRACT

Novel cyclic monomers leaving two functional groups capable of undergoing condensation reactions to form amide, urea or urethane linkages and at least one photo or radiation-reactive group are condensed with cyclic comonomers to form a soluble, substantially-linear condensation pre-polymer. A solution of the prepolymer is applied to a substrate and the solution is evaporated off to form a film or foil. The photo or radiation-sensitive layer or foil is exposed or irradiated through a pattern, the unexposed or unirradiated part is dissolved or stripped off, and the relief structure which remains is annealed if necessary. The relief structures obtained are distinguished particularly by the sharpness of their edges, good mechanical and chemical properties as well as good insulating properties. They are suited particularly for the preparation of miniaturized insulating layers.

10 Claims, 2 Drawing Figures

METHOD FOR THE PREPARATION OF RELIEF STRUCTURES

This invention is concerned with a method for the preparation of relief structures consisting of highly heat-resistant polymers.

It is known that polyamidopolycarboxylic acids can be sensitized as soluble prepolymers for thermally stable polyimides for photo-cross linking by the addition of dichromates; see Polymer Engineering and Science, vol. 11, p. 426 to 430 (1971). However, their application as a negative photo-resistant, which is annealed after exposure and development for the preparation of highly heat-resistant relief structures, is made very difficult by the fact that the solutions and films of these photsensitized polyamidopolycarboxylic acids are very unstable and accordingly must be processed immediately after preparation. The unsensitized polyamidopolycarboxylic acids also have only limited storage stability even if cooled. Furthermore, the highly heat-resistant polyimides prepared from the sensitized substances have a considerable content of inorganic salts, which limits their possible applications, particularly as insulated materials in electrotechnology.

It is further known that relief structures can be produced from polyamideopolycarboxylic acid films by means of the photo-lacquer technique and that the film material can then be transformed into polyimides through annealing; see German Auslegeschrift No. 1,764,977. The limitation as to storage stability of the polyamidopolycarboxylic acid applies here to the same extent. Furthermore, only limited resolution and moderate edge definition can be obtained when dissolving the unexposed portions of the film because of the tendency of undercutting.

It has been found that the disadvantages mentioned above can be avoided if, for the preparation of relief structures consisting of highly heat-resistaant polymers, one uses as soluble prepolymers poly-addition or poly-condensation products of polyfunctional carbocyclic and/or heterocyclic compounds which contain at least two chemical groups suitable for addition or condensation reactions and in addition, in ortho- or peri-position thereto, contain organic photo- or radiation groups R* which are bound to carboxyl groups in ester-fashion.

R*, as used herein, is defined as an organic residue with a photo- or radiation-induced dimerizable or polymerizable multiple bond, preferably an olefinically-unsaturated double bond.

The soluble polymers comprise carbocyclic and/or heterocyclic moieties which are linked together with amide urea or urethane linkages and which, in ortho- or peri-position relative to the amide, urea, urethane linkages, contain organic photo- or radiation-reactive R* groups. The polymers, which can be cyclized to form new heterocyclic chain links by splitting off the photo- or radiation-reactive R* upon heating, are exposed or irradiated through a pattern, preferably a negative pattern, in the form of films on a substrate or in the form of foil. The exposure is preferably made with ultraviolet light. The unexposed or unirradiated portions are subsequently dissolved or stripped off to leave highly heat-resistant relief structures remain. In a further embodiment of the method, the relief structures obtained are subsequently annealed. In this process, the bonds from the polymer chains to the photo- or radiation crosslinkable and photo- or radiation crosslinked groups are ruptured, and through cyclizing, ladder or step-ladder polymers with heterocyclic chain links exhibiting highly heat-resistant properties are produced to an increased degree.

The processes of this invention are further illustrated in FIGS. 1 and 2, wherein.

Figure 1:
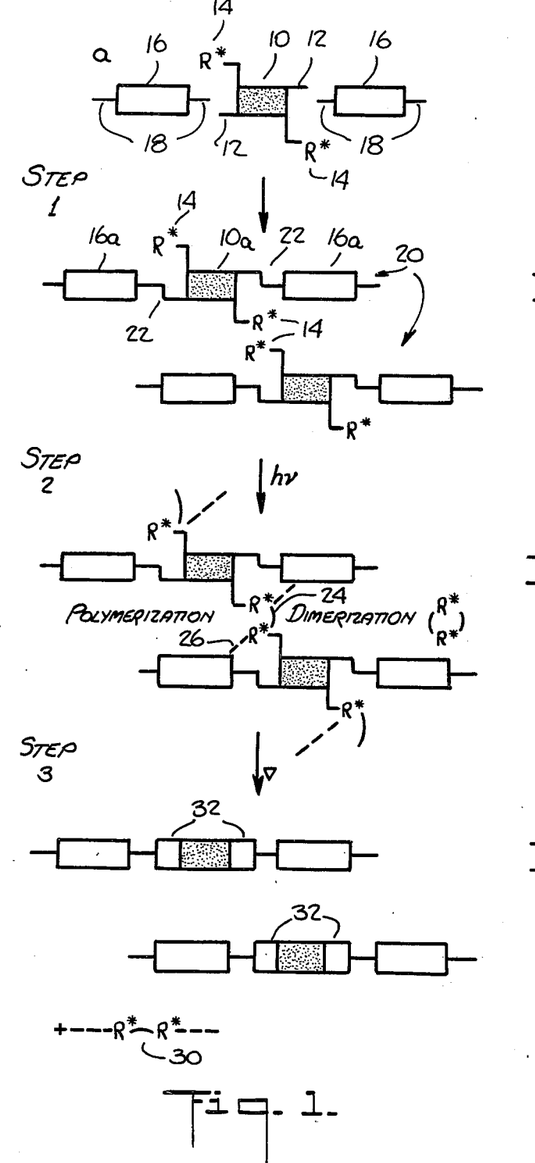
FIG. 1 is a schematic diagram illustrating one embodiment of the process of this invention.

With reference to FIG. 1, First Ring Compound 10, having two poly-condensation radicals 12 and two R* groups 14, is reacted in Step 1 with Second Ring Compound 16, having two polycondensation radicals 18 which react with radicals 12 of First Ring Compound 10 to form linear polymer 20 comprised of First Ring Compound residues 10a bonded to Second Ring Compound residues 16a through amide, urea or urethane linkages 22 and having pendant R* groups 14. In step 2, linear polymer 20 is irradiated whereby R* groups 14 on adjacent polymer chains react to form cross-links 24. On heating of the cross-linked structure in Step 3, the original bonds of the R* groups to the polymer chains are broken, resulting in the formation of R* residues 30, which are split off, and in the formation of new heterocyclic rings 32 bonded to the original cyclic nucleus of the First Ring Compound through reaction with the amide, urea or urethane linkages 20.

Figure 2:
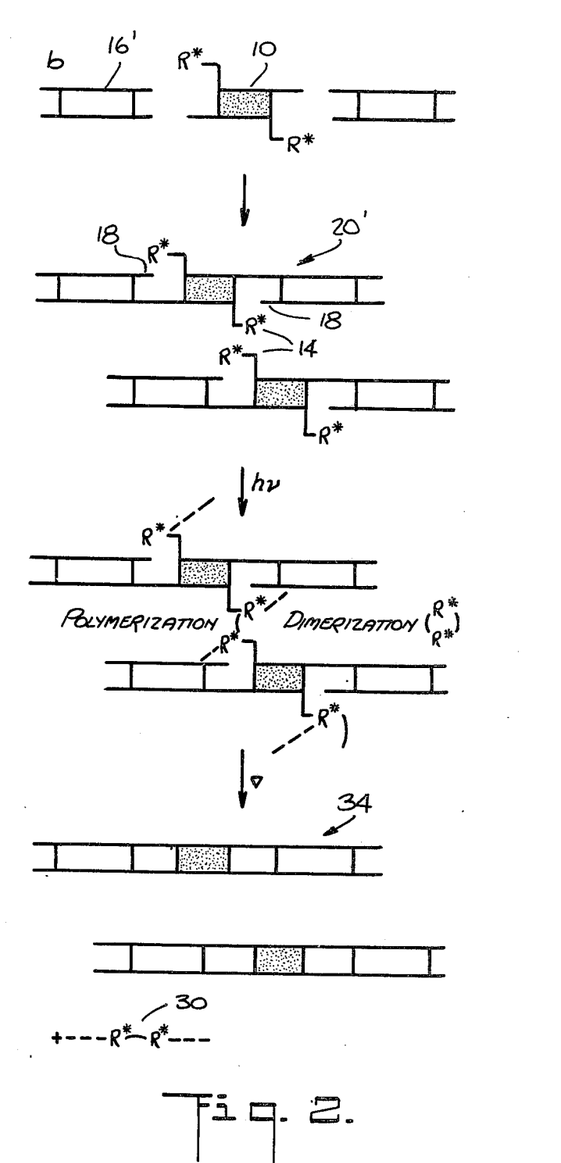
FIG. 2 is a schematic diagram illustrating a second embodiment of the process of this invention.

In the embodiment shown in FIG. 2, First Ring Compound 10 is reacted with a tetrafunctional Second Ring Compound 16' in Step 1 to form a linear condensation polymer 20' having pendant R* groups 14 and pendant groups 18. On exposure to Radiation in Step 2, cross-linking occurs as before. In this case, however, when the cross-linked resin is annealed in Step 3 to form R* residues 30, cyclization occurs with the pendent reactive groups 18 derived from Second Ring Compound 16' to form a cyclic, ladder-like structure 34.

To prepare the soluble prepolymers used according to the invention, which are stable for storage at room temperature, a tri- or tetrafunctional compound designated as a First Ring Compound is poly-added or poly-condensed with a Second Ring Compound. The First Ring Compound has an at least partially cyclic structure which contains (a) two chemical functions capable of condensation or addition reactions, and (b) one to two further unsaturated carboxylic-acid ester functions in ortho- or peri-position thereto. The Second Ring Compound is an at least partially cyclically structured, di- or tetrafunctional compound which contains, besides the two chemical functions (a) capable of poly-condensation or poly-addition reactions, two further chemical functions in ortho- or peri-position which participate during the annealing in a subsequent cyclizing reaction, which proceeds under separation of R*OH.

Examples of suitable combinations of chemical functions capable of condensation or addition are given in the following schematic tabulation:

| Case No. | Chemical Functions | First Ring Compound | | Second Ring Compound |
|---|---|---|---|---|
| 1) | a | —COCl<br>—COCl | a | —NH$_2$<br>—NH$_2$ |
|  | b | —COOR*<br>(—COOR*) | — | — |
| 2) | a | —COOH<br>—COOH | a | —NCO<br>—NCO |
|  | b | —COOR*<br>(—COOR*) | — | — |
| 3) | a | —NH$_2$<br>—NH$_2$ | a | —COCl<br>—COCl |
|  | b | —COOR*<br>(—COOR*) | — | — |
| 4) | a | —NCO<br>—NCO | a | —COOH<br>—COOH |
|  | b | —COOR*<br>(—COOR*) | — | — |
| 5) | a | —NH$_2$<br>—NH$_2$ | a | —NCO<br>—NCO |
|  | b | —COOR*<br>(—COOR*) | — | — |
| 6) | a | —OH<br>—OH | a | —NCO<br>—NCO |
|  | b | —COOR*<br>(—COOR*) | — | — |

( ) indicates the functional group is optional.

In Case 1, the First Ring Compound is a bis-acid chloride containing one or two R* ester groups while the Second Ring Compound is a diamine. Alternatively, the First Ring Compound can be a diamine and the Second Ring Compound can be a bis-acid chloride (Case No. 3). In Case No. 2, the First Ring Compound is a diacid having one or two R* ester groups, while the Second Ring Compound is a diisocyanate, while in Case No. 4 the carboxyl and isocyanate groups are exchanged. Cases No. 5 and No. 6 are similar to Case No. 2, except that the carboxyl groups of the First Ring Compound of Case No. 2 are replaced by amino groups (Case No. 5), or hydroxyl groups (Case No. 6).

For the preparation of relief structures according to the invention, polymers of the following classes of substances are particularly well suited:

Polyisoindolquinazolindiones as derived from comonomers of Case 1

Polyimides, polyamidimides and polyester imides derived from comonomers of Cases 1 or 2

Poly-1,3-oxazine-6-ones derived from comonomers of Cases 3 or 4

Poly-1,3-quinazoline-2,6-diones derived from comonomers of Case 5, and

Polybenz-1,3-oxazindiones-2,4 derived from comonomers of Case 6

These are examples of highly temperature-resistant polymers which can be prepared according to the invention via photo-interlinkable, soluble intermediate stages.

The primary soluble prepolymers obtained through polycondensation contain photo- or radiation-reactive organic groups R* which are bound to carboxyl functions in ester-fashion and can dimerize or homo- or co-polymerize upon exposure to high-energy light or other radiation, possibly splitting off fragments, and thus cause insolubility, depending on the cross-linkage.

Ultra-violet light is preferred, but irradiation with ionizing radiation, X-rays or accelerated electrons is also possible.

As noted previously, the First Ring Compound is a cyclic structure having two functional groups capable of forming amide, urea or urethane linkages and at least one R* group bonded to the compound through an ester linkage. These compounds may be represented by the formula:

wherein X is a carbocyclic and/or heterocyclic nucleus, Y is a condensable functional group such as carboxyl, carbonyl chloride, amine, isocyanate or hydroxyl; R*X is as defined above; and x is 1 or 2.

These compounds are readily derived from known starting materials. For example, pyromellitic anhydride is a convenient starting material for compounds wherein Y is carboxyl or carbonylchloride. Still other starting materials will be apparent to those of ordinary skill in the art.

The —CO$_2$R* radical is formed by conventional esterification techniques, as by reaction of an aromatic acid, acid anhydride or acid chloride with an alcohol of the formula R*OH.

X is preferably an aromatic residue such as a benzene residue, a pyridine residue or a residue of a biphenyl compound for the formula:

where M is 0, CH$_2$ or SO$_2$ and z is o or 1. When X is a benzene residue, preferred compounds are those of the formula:

wherein Y and R* are as defined above. When an X is a biphenyl residue, preferred compounds are those of the formula:

wherein Y and R* are as defined above and Y and R* are on adjacent carbons.

Suitable residues R* are known photo- or radiation-reactive organic groups, which, if necessary, with stabilization, are stable in the absence of light under the applicable preparation conditions for the poly-functional starting compounds, the poly-condensation or poly-addition conditions and under storage at room temperature. Suitable alcoholic or phenolic, photo- or radiation reactive starting compounds R*OH for the esterification are, for instance:

and wherein in the above formulas:
R is hydrogen or hydroxyalkyl;
R$^1$ is alkyl, phenyl, alkoxyphenyl or halophenyl;
R$^2$ is hydrogen, chlorine, alkyl or alkoxy;
R$^3$ is hydroxyalkyl;
R$^4$ is a carbocyclic or heterocyclic residue bonded through a ring carbon; and
n is 1 or 2.
R* preferably is allyl or a radical containing, the cinnamoyl moiety, with allyl being especially preferred.

The alkyl and alkoxy groups preferably are linear or branched chain alkyl or alkoxy groups from 1 to about 6 carbons, especially methyl, ethyl and propyl, and the corresponding alkoxy groups. Hydroxyalkyl groups comprehend hydroxy-substituted linear or branched alkyl groups of 2 to 6 carbons, especially hydroxyethyl and hydroxy propyl. Halogen substituents include chlorine, bromine or iodine, with chlorine being preferred. Carbocyclic residues comprise phenyl, biphenyl, naphthyl and the like, which may be substituted with alkyl, halogen, or other inert substituents. Heterocyclic residues are those corresponding to the aromatic residues, wherein one or more carbons is replaced by nitrogen, including residues of pyridine, quinoline, pyrimidine and the like. Preferred prepolymers are preferred from a First Ring Compound comprising a tetrafunctional benzene compounds having two unsaturated ester substituents and either two carboxylic acid, two carboxylic acid chloride or two hydroxyl substituents.

The Second Ring Compound is a polyfunctional, i.e., di- or tetrafunctional compound having two functional groups capable in the condensation with the condensable functional groups of the First Ring Compound to form amide, urea or urethane linkages. The Second Ring Compound also may have two functional groups which, upon heating of the polymer of this invention to liberate R*OH, react with the carbonyl group formerly attached to OR* to form a cyclic structure. The Second Ring Compound may be represented by the formula:

where D is a carbocyclid or hetero-cyclic nucleus; E is a condensable group capable of forming amide, urea or urethane linkages, F is a group capable of reacting with carbonyl formed upon releasing R*OH on heating; and y is 0 or 2. Preferred compounds are those wherein y is 0; D is phenylene, a pyridinylene or a diphenyl group of the formula where M is O, SO$_2$ or CH$_2$; z is o or 1; and E is carboxyl, carbonyl chloride, amino or isocyanate.

The prepolymers are obtained by condensation polymerization of the First and Second Ring Compounds to afford linear polyamides, polyurea or polyurethanes. The conditions for effecting such reactions are well-known, and will not be further detailed here. Suffice it to say that suitable prepolymers have been obtained by reacting approximately equi-molar quantities of a First Ring Compound with a Second Ring Compound in a suitable solvent at temperatures sufficient to effect the polycondensation. Highly elevated temperatures sufficient to cause scission of the OR* group or vinyl polymerization should be avoided.

The resulting prepolymer is a substantially linear polyamide, polyurea or polyurethane comprised of cyclic nuclei bonded to each other through amid, urea or urethane linkages and having pendant —CO$_2$R* substituents. The prepolymers have repeating units of the formula:

wherein X, D, F, R*, x and y are as previously defined and G is an amide, urea or urethane linkage formed by reaction of the functional groups defined by Y and F above.

The resulting linear condensation prepolymer is then formed into a film or foil by applying a solution of the prepolymer to a substrate and evaporating off the solvent. The dried film or foil is then subjected to imagewise radiation with light or other forms of radiation to effect cross-linking through the pendant R* groups. In order to increase the speed of cross-linking during Step 2, commonly used photo- initiators and/or sensitizers can be employed; see Industrie Chimique Belge vol. 24, p. 739 to 64 (1959) or Light-sensitive Systems by J. Kosar, John Viley & Sons, Inc., New York 1965, p. 143 to 146 and 160 to 188. The soluble polymer chains can furthermore be combined for this purpose with other light- or radiation-sensitive compounds capable of copolymerization. The interlinkage caused by exposure to light or radiation can optionally be supplemented by annealing at temperatures, at which no purely thermal interlinking or cyclization takes place yet.

A particular advantage of the soluble prepolymers used according to this invention is that partial cross-linking of the photo- or radiation-reactive residues R*, i.e., incomplete cross-linking of the exposed or irradiated residues R*, leads to relief structures with well-defined edges and sufficient insolubility of the exposed or irradiated film or foil portions. The compounds liberated during a subsequent annealing in a cyclizing reaction can easily be volatized. Only few inter-linking bridges remain. These can be further taken down thermally, as required, and can likewise be removed. Easily evaporized starting compounds R*OH have been found particularly advantageous for the esterification, such as, for instance, allyl alcohol. The allyl ester groups cause, particularly in combination with compounds which contain one or several N-substituted maleinimde groups, rapid interlinking of the polymer chain with UV exposure.

Highly suited sensitizers and/or initiators are, for instance, Michler's ketone and/or benzoin ether, 2-tertiarybutyl-9, 10-anthraquinone, 1,2-benz-9, 10-anthraquinone, and 4, 4'-bis (diethylamino)benzophenone.

The photo- or radiation-interlinkable soluble prepolymers used according to the invention can be processed on a substrate from solution into uniform coatings or foil with excellent mechanical properties and, in most case, good adhesion. The layers or foils can be converted in a manner known per se through light exposure or irradiation and subsequent dissolving or stripping of unexposed or not irradiated portions into negatives with a relief structure having extremely well-defined edges. These highly temperature-stable, photo- or radiation cross linked polymers can be transformed by a brief anneal into polymers, known per se, with further increased thermal stability.

The method according to the invention this makes possible the simple ans reliable preparation of highly temperature-resistant and, if desired, miniaturized relief structures with sharp edges and good insulating properties, i.e., high stability against aging high electric surface and bulk resistivity, low water absorption and swelling, and excellent mechanical and chemical properties, particularly chemical resistance to printing inks. The adhesion of the generated patterns of insulating material to various substrates can further be improved by common adhesion agents, such as, for instance, the organic silicon compounds vinyl triethoxy silane, vinyl trimethoxy silane, γ-methacryloxy propyl trimethoxy silane. The patterns can be provided in a manner known per se with seed layers for producing highly adherent electrodeposited coatings; they can furthermore be coated with highly adherent metallic and other evaporated layers. Conditions for broad and technically advantageous application of the method according to the invention therefore exist.

Thus, the method according to the invention can be used to advantage for the preparation of passivating layers on semi-conductor components of solder-protection varnish layers on multi-layer circuits, of miniaturized layer circuits, of printed circuits with electrodeposited conductors, of miniaturized layers of insulation on electrically conducting and/or semi-conducting and-/or insulating base materials, of optically interrogated image storage devices as well as of etch resists or plating resists, preferably without subsequent annealing. The method according to the invention is, moreover, also usable to advantage for other, already known applications, as described in the German Auslegeschrift No. 1,295,192, column 3, such as for the preparation of high-quality printing forms.

The invention will be illustrated by the following examples:

EXAMPLE 1

Pyromellitic Acid

Diallyl Ester Bis-acid Chlorides (First Ring Compound)

and

A mixture of 87.2 parts by weight of pyromellitic acid dianhydride, were shaken with 400 parts by volume of allyl alcohol, and 0.4 parts by weight of p,p'-bis(dimethylamino)diphenylmethane was shaken for 26 hours at room temperature; then, excess allyl alcohol was distilled off in a water-jet vacuum.

According to the IR spectrum, ($\nu$ carboxylic acid at 3.75 – 4 $\mu$; $\nu$ aromatic ester at 8 $\mu$ and 9; $\nu$ allyl at 6.1 $\mu$ and 10.1 $\nu$) and the acid number, the residue consisted of heretofore unknown pyromellitic acid diallyl esters. A mixture of the esters with 200 parts by weight of thionyl chloride and 5 parts by volume of dimethyl formamide was allowed to stand at room temperature for 1 hour and then was boiled for 3 hours under reflux. Excess thionyl chloride was distilled off in a water-jet vacuum to yield the novel pyromellitic acid diallylester-bis-acid chlorides, which were characterized by means of the IR spectrum ($\nu$ acid chloride at 5.5 $\mu$: $\nu$ aromatic ester at 5.8 $\mu$ and at 8 $\mu$; $\nu$ allyl at 6.1 $\mu$ and 10.1 $\mu$).

Polyamidopolycarbonicacid Allyl Ester Prepolymer

The First Ring Compound produced as described above was dissolved in 350 parts by volume of absolute dimethyl acetamide and the solution was added drop-wise, while stirring and in the absence of moisture, to a solution of 80 parts by weight of p,p'-diaminodiphenyl ether (the Second Ring Compound) in 400 parts by volume of absolute dimethyl acetamide cooled to 0°C, without allowing the reaction mixture temperature to rise above 20°C. After the addition, the reaction mixture was further stirred for 1 hour at room temperature and then the solution was reacted with 5 parts by volume of aniline, stirred for 5 minutes and filtered. The prepolymer reaction product was precipitated by adding it drop-wise in 4 liters of boiling water, washed with hot water as well as a 1:1 acetone-water mixture, and dried at 80°C in vacuum. The IR spectrum of the prepolymer showed that it was the polyamidopolycarboxylic acid allyl ester was produced ($\nu$ aromatic amide at 3.1 $\mu$ and 6 $\mu$; $\nu$ aromatic ester at 5.8 and 8.1 $\mu$; $\nu$ allyl at 10.1 $\mu$).

Relief Structure

A solution of 5 parts by weight of the thus-produced soluble prepolymer, 0.5 parts by weight of maleinanil, 0.025 parts by weight of Michler's ketone and 0.025 parts by weight of benzoin ethyl ether dissolved in 20 parts by volume of dimethylformamide was filtered and centrifuged on copper foils to make uniform films. The films are 7 $\mu$ thick after evaporation of the solvent and exhibited excellent mechanical properties (scratch-proof, elastic), with excellent adhesion to the substrate. The films were irradiated with a 500-W high-pressure mercury lamp at a distance of 23 cm through a line raster for 3 minutes, then brushed for 70 seconds while immersed in a bath of solvent consisting of a 1:1 mixture of dimethyl formamide and ethanol, and were subsequently washed with ethanol. A relief image having a resolution of better than 40 μ was obtained with good edge definition. A solution of 5 parts by weight of the soluble prepolymer, 0.2 parts by weight of maleinanil and 0.05 parts by weight of Michler's ketone dissolved in dimethyl acetamide, produced as described, was processed into 4-μ thick films and exposed through a line raster for 30 seconds. The films were subsequently annealed for 1.5 hours at 160°C and brushed for 90 seconds while immersed in a bath of solvent consisting of a 5:2 mixture of dimethyl formamide and methanol. A resolution of better than 40 μ was obtained with good edge definition.

The samples obtained as described in paragraphs (a) and (b) were annealed for 3 hours at 180°C or 15 minutes at 350°C. The resolution and edge definition remained unchanged, and the relief structure then exhibited the excellent thermal, mechanical, electrical and chemical properties of the polyimide poly(diphenyloxidepyromellitimide). The IR spectrum of the annealed samples showed the bands at 5.6 μ typical of the imide structure.

EXAMPLE 2

Pyromellitic acid diallyl ester bis-acid chlorides produced as described in Example 1 were reacted with p,p'-diaminodiphenyl methane as the Second Ring Compound employing the procedure described in Example 1 to form a soluble prepolymer.

The IR spectrum of the prepolymer showed the bands characteristic of a polyamidopolycarboxylic acid allyl ester. ($\nu$ aromatic amide at 3.1 μ and 6 μ; $\nu$ aromatic ester at 5.8 μ and 8.1 μ; $\nu$ allyl at 10.1 μ).
Relief Structure A solution of 10 parts by weight of soluble prepolymer, 1 part by weight of maleinanil and 0.1 part by weight of Michler's ketone dissolved in 20 parts by volume of N-methylpyrrolidone was processed, as described in Example 1, into 8-μ thick films on aluminum foil, irradiated for 5 minutes through a line raster and immersed for 30 seconds in a bath of solvent consisting of a 1:1 mixture of dimethyl formamide and ethanol. A resolution of better than 40 μ was obtained with good edge definition.

The samples obtained were annealed for 3 hours at 180°C or 15 minutes at 350°C. The resolution and edge definition remained unchanged, and the relief structure then exhibited the excellent thermal, mechanical, electrical and chemical properties of polydiphenylmethanepyromellitimide). The IR spectrum of the annealed product exhibited the bands at 5.6 μ typical of the imide structure

EXAMPLE 3

The procedure of Example 1 was repeated, except that p,p'-diaminodiphenyl sulfone was substituted for the p,p'-diaminodiphenyl ether as the Second Ring Compound. The IR spectrum of the resulting prepolymer exhibited the bands typical of the polyamidopolycarboxylic-acid allyl ester ($\nu$ aromatic amide at 3.1 μ and 6 μ; $\nu$ aromatic ester at 5.8 μ and 8.1 μ; $\nu$ allyl at 10.1 μ).
Relief Structure A solution of 5 parts by weight of the soluble prepolymer, 0.25 parts by weight of maleinanil and 0.05 parts by weight of Michler's ketone dissolved in 15 parts by volume of dimethyl formamide/toluene (60:40) and processed, as described in Example 1, into 3-μ thick films on aluminum foil, irradiated for 5 minutes through a line raster and immersed for 1 minute in a bath of solvent consisting of a 1:1 mixture of diethyl formamide and ethanol. A resolution of better than 40 μ was obtained with good edge definition. The samples obtained were annealed for 3 hours at 180°C for 15 minutes at 350°C. The resolution and edge definition remained unchanged, and the relief structures then exhibited the excellent thermal, mechanical, and chemical properties of the polyimide poly(diphenylsulfonepyromellitimide). The IR spectrum of the annealed samples exhibited the bands at 5.6 μ typical of the imide structure.

EXAMPLE 4

The procedure of Example 1 was repeated, except that 2,4-diaminopyridine was substituted for the p,p'diaminodiphenyl ether as the Second Ring Compound to form a prepolymer, whose IR spectrum exhibited the bands characteristic of the polyamidopolycarboxylic-acid allyl ester ($\nu$ aromatic amide at 3.1 μ and 5.9 μ; $\nu$ aromatic ester at 58.0 μ and 8 μ; $\nu$ allyl at 10.1 μ).
Relief Structure

A solution of 5 parts by weight of the soluble prepolymer, 0.5 parts by weight of maleinanil and 0.1 parts by weight of Michler's ketone dissolved in 10 parts by volume of dimethyl formamide was processed, as described in Example 1, into 3-μ thick films on aluminum foil. The films were irradiated for 10 minutes through a line raster and immersed for 3 seconds in a bath of solvent consisting of dimethyl formamide-ethanol (1:1). A resolution of better than 40 μ was obtained with good edge definition. The samples obtained were annealed for 3 hours at 180°C. The resolution and edge definition remained unchanged, and the relief structures then consisted, according to the IR spectrum, ($\nu$ imide at 5.6 μ) of the polyimide poly(pyridinepyromellitimide) and exhibited the pecular polyimide properties.

EXAMPLE 5

Pyromellitic Acid Bis(polypropyleneglycol monocinnamate) Ester Bis-acid Chlorides (First Ring Compound)

and wherein R is or

A mixture of 148 parts of cinnamic acid, 64 parts by weight of propylene oxide, 2 parts by weight of p,p'-bis(dimethylamino)diphenylmethane and 0.1 parts by weight of hydroquinone was heated under reflux in 500 parts by volume of benzene for 28 hours. The reaction solution was washed with aqueous sodium bicarbonate solution and was dried. The reaction mixture of the propyleneglycolmonocinnamates distilled over at 126° to 128°C/0.1 Torr. A 45.2 part by weight portion of the liquid distillate component was shaken with 21.8 parts by weight of pyromellitic dianhydride and 0.1 part of p,p'-bis(dimethylamino)diphenylmethane in 50 parts by volume of absolute acetone for 8 days at room temperature, and the solvent was then distilled off in a water-jet vacuum. The resulting novel acid pyromellitic acid-bis(propyleneglycolmonocinnamate)-esters were identified by means of their IR spectrum ($\nu$ carboxylic acid at 3.75 to 4 $\mu$; $\nu$ aromatic ester at 8 $\mu$; $\nu$ cinnematic at 6.1 $\mu$ and 13 $\mu$) and the acid number. They were left standing with 200 parts by weight of thionyl chloride and 5 parts by volume of dimethylformamide for 1 hour at room temperature and then boiled for 3 hours under reflux. Excess thionyl chloride was distilled off in a water-jet vacuum. The pyromellitic acid-bis(propyleneglycolmonocinnamate)ester-bis-acid chlorides remaining as the residue were characterized by means of their IR spectrum ($\nu$ acid chloride at 5.5 $\mu$; $\nu$ carboxylic acid - none; $\nu$ aromatic ester at 5.8 $\mu$ and 8 $\mu$; $\nu$ cinnematec at 6.1 $\mu$ and 13 $\mu$).

Soluble Prepolymer

The thus-obtained reaction product was dissolved in 85 parts by volume of absolute dimethyl acetamide and added dropwise, as described in Example 1, to a solution of 20 parts by weight of p,p'-diaminodiphenyl ether in 90 parts by volume of absolute dimethyl acetamide. The resulting reaction product was precipitated in cold water. Its IR spectrum exhibited the bands characteristic of the polyamidopolycarboxylic acid (propyleneglycolmonocinnamate) ester ($\nu$ aromatic amide at 3.1 $\mu$ and 6 $\mu$; $\nu$ aromatic ester at 5.8 $\mu$ and 8.1 $\mu$; $\nu$ cinnemate at 6.1 $\mu$ and 13 $\mu$).

Relief Structure

A solution of 5 parts by weight of the soluble prepolymer, 0.5 parts by weight of maleinanil, 0.05 parts by weight of Michler's ketone and 0.05 parts by weight of benzoinethyl ether dissolved in 10 parts by volume of dimethyl formamide was processed, as described in Example 1, into 4-$\mu$ thick films on aluminum foil, irradiated for 60 minutes through a line raster and immersed for 9 seconds in a bath of solvent consisting of a mixture of dimethyl formamide-ethanol (1:2.5). Relief structures with sharp edges were obtained. The samples obtained were annealed for 3 hours at 180°C. The edge definition remained unchanged and the relief structures then consisted, according to their IR spectrum, of the polyimide poly(diphenyloxide pyromellitimide) ($\nu$ imide at 5.6 $\mu$) and showed the peculiar polyimide properties.

EXAMPLE 6

Pyromellitic Acid Bis(Polypropyleneglycol mono-α-cyanocinnamate) Ester Bis-acid Chlorides (First Ring Compound)

and wherein R is or

A mixture of 81.4 parts by weight of α-cyano-cinnamic acid, 29 parts by weight of propylene oxide, 1.1 parts by weight of p,p'-bis(dimethylamino)diphenylmethane and 0.1 parts by weight of hydroquinone were heated for 17 hours in 250 parts by volume of benzene under reflux. The reaction solution was washed with aqueous sodium bicarbonate solution and was dried. The reaction mixture of the proplyeneglycolmono-α-cyano-cinnamate distilled over at 155° to 160°C/0.1 Torr. Melting point CCl$_4$/petroleum benzine boiling point 40° to 60°C 1:1) 80°C.

A 35.3 part by weight portion of propyleneglycolmono-α-cyanocinnemate was shaken with 5.5 parts by weight of pyromellitic acid anhydride and 0.05 parts by weight of p,p'-bis(dimethylamino)diphenyl methane in 150 parts by volume of absolute acetone for 3 days at room temperature. After adding 100 parts by volume of ethanol, the addition of alcoholic hydroxyl groups to pyromellitic acid dianhydride was completed by shaking of 24 hours at room temperature. The solvent and the excess alcohol were distilled off in a water-jet vacuum. The thus-produced novel pyromellitic acid-bis(-propyleneglycol-mono-α-cyanocinnamate) esters were identified by means of their IR spectrum ($\nu$ carboxylic acid at 3.75 to 4 $\mu$; $\nu$ aromatic ester at 8 $\mu$; $\nu$ α-cyanocinnamate at 4.5 $\mu$ and 13 $\mu$) and the acid number. The reaction mixture was let stand with 70 parts by volume of thionyl chloride and 5 parts by volume of dimethyl formamide for 1 hour at room temperature, and was then boiled for 3 hours under reflux. Excess thionyl chloride was distilled off in a water-jet vacuum. The pyromellitic-acid-bis(propyleneglycol-α-cyanocinnamate)ester-bis-acid chlorides contained in the residue were characterized by means of their IR spectrum ($\nu$ acid chloride at 5.5 $\mu$; $\nu$ carboxylic acid none; $\mu$ aromatic ester at 5.8 $\mu$ and 8 $\mu$; $\nu$ cyanocinnamate at 4.5 $\mu$ and 13 $\mu$).

Soluble Prepolymer

The resulting reaction product was dissolved in 50 parts by volume of absolute dimethyl acetamide and added dropwise, as described in Example 1, to a solution of 5 parts by weight of p,p'-diaminodiphenyl ether (the Second Ring Compound) in 50 parts by volume of absolute dimethyl acetamide. The resulting reaction product was precipitated in cold water, washed twice with H$_2$O/methanol and three times with CCl$_4$/n-hexane/methanol (1:1:1) and was dried. The IR spectrum of the thus-isolated prepolymer exhibited the bands characteristic of the polyamidopolycarboxylic acid (propyleneglycol-mono-α-cyanocinnamate) ester ($\nu$ aromatic amide at 3.1 $\mu$ and 6 $\mu$; $\nu$ aromatic ester at 5.8 $\mu$ and 8 $\mu$; $\nu$ α-cyanocinnamate at 4.5 $\mu$ and 13 $\mu$).

Relief Structure

A solution of 5 parts by weight of the soluble prepolymer stage and 0.05 parts by weight of Michler's ketone dissolved in 10 parts by volume of dimethyl formamide was processed, as described in Example 1, into 4-$\mu$ thick foils on aluminum foil, irradiated for 120 minutes through a line raster and immersed for 10 seconds in a bath of solvent consisting of a mixture of dimethyl formamide/ethanol (1:1). Relief structures with sharp edges were obtained. The samples obtained were annealed for 3 hours at 180°C. The edge definition remained unchanged, and the relief structures then consisted, according to the IR spectrum ($\mu$ imide at 5.6 $\mu$) of the polyimide poly(diphenyloxide pyromellitimide) and exhibited the peculiar polyimide properties.

EXAMPLE 7

Pyromellitic Acid Diallyl Esters (First Ring Compound)

and

A 21.8 part by weight portion of pyromellitic acid dianhydride was stirred with 11.6 parts by weight of allyl alcohol in 100 parts by weight of absolute dimethyl formamide for 8 days at room temperature. The reaction was monitored by means of the acid number and was then about 95% complete.
Soluble Prepolymer The solution of the thus-produced diallyl ester in dimethyl formamide was reacted with 100 parts by weight of absolute dimethyl acetamide and 0.06 parts by weight of 1,4-diazabicyclo[2.2.2]octane and added drop-wise, while stirring and in the absence of moisture, within 30 minutes at 55° to 60°C to a solution of 25 parts by weight of p,p'-diphenylmethane diisocyanate (Second Ring Compound) in 190 parts by weight of absolute dimethyl acetamide. The mixture was then stirred for another 60 minutes at 55° to 60°C and 7 hours at 75°C. The resulting reaction product was precipitated in cold water, washed with water and methanol/water (1:1) and dried at 80°C in vacuum. The IR spectrum of the thus-obtained prepolymer exhibits the bands characteristic of the polyamidopolycarboxylic-acid allyl ester ($\nu$ aromatic amide at 3 $\mu$; $\nu$ aromatic ester at 5 $\mu$ and 8.1 $\mu$; $\nu$ allyl at 10.1 $\mu$).
Relief Structure A solution of 5 parts by weight of the soluble prepolymer, 0.5 parts by weight of maleinanil and 0.05 parts by weight of Michler's ketone dissolved in 10 parts by volume of dimethyl formamide was processed, as described in Example 1, into 4-$\mu$ thick films on aluminum foil, irradiated for 10 minutes through a line raster and immersed for 90 seconds in a bath of solvent consisting of a mixture of dimethyl formamide/ethanol (1:2). A resolution of better than 40 $\mu$ was obtained with good edge definition. The samples obtained were annealed for 3 hours at 180°C. The resolution and edge definition remained unchanged, and the relief structures consisted, according to their IR spectrum ($\nu$ imide at 5.6 $\mu$) of the polyimide poly(diphenylmethanepyromellitimide) and exhibited the peculiar polyimide properties.

EXAMPLE 8

Bis(p-hydroxyphenyl)-methane-3,3'-dicarboxylic Acid Diallyl Ester (First Ring Compound)

A mixture of 72 parts by weight of bis(p-hydroxyphenyl) methane-3,3'-dicarboxylic acid and 5 parts by weight of p-toluol sulfonic acid was heated with 100 parts by volume of allyl alcohol for 15 hours under reflux. After addition of 100 parts by volume of benzene, the reaction water was removed by azeotropic distillation, using a water separator, over a period of 24 hours. Subsequently, benzene was distilled off, the residue was reacted with 100 parts by volume of allyl alcohol and heated for another 2.5 days under reflex. After adding 100 parts by volume of benzene, the reaction water was again removed, as described, from the solution over a period of 8 days. The novel diallyl ester reaction product distilled over at about 70°C/0.2 Torr. It was identified by means of its IR spectrum ($\nu$ phenolic hydroxyl at 2.9 $\mu$; $\nu$ aromatic ester at 5.9 $\mu$ and 8 $\mu$; $\nu$ allyl at 6.1 $\mu$, 10.1 $\mu$ and 10.8 $\mu$).
Soluble Prepolymer A solution of 13.2 parts by weight of p,p'-diphenyl methane diisocyanate (the Second Ring Compound) dissolved in 50 parts by volume of dimethyl acetamide was added drop-wise over a period of 15 minutes, while stirring, to a solution of 15.3 parts by weight of the First Ring Compound and 0.014 parts by weight of 1,4-diazabicyclo[2.2.2] octane in 50 ml of absolute dimethyl acetamide at −10°C. The reaction solution was stirred for another 1 hour at 0°C, 1.5 hours at 22°C, 30 minutes at 43°C and 30 minutes at 75°C. The resulting prepolymer reaction product was precipitated in methanol and dried at 50°C. The IR spectrum exhibited the bands characteristics of the polyurethanepolycarboxylic-acid allyl ester ($\nu$ NH-urethane at 3 $\mu$; $\nu$ aromatic ester at 5.8 $\mu$ and 8.2 $\mu$; $\nu$ allyl at 6.1 $\mu$ and 10.1 $\mu$ ).
Relief Structure A solution of 2.2 parts by weight of the soluble prepolymer, 0.22 parts by weight of maleinanil and 0.022 parts by weight of Michler's ketone dissolved in 8 parts by weight of dimethyl formamide was processed, as described in Example 1, into 5-$\mu$ thick films on aluminum foil, irradiated for 5 minutes through a line raster and immersed for 30 seconds in a bath of solvent consisting of a mixture of dimethyl formamide/ethanol (1:1). A resolution of better than 40 $\mu$ was obtained with good edge definition. The samples obtained were annealed for 2 hours at 240°C. The resolution and edge definition remained unchanged, and the relief structure then exhibited the excellent thermal, mechanical and chemical properties of the polybenz-1,3-oxazinediones-2,4. In the IR spectrum of the annealed samples, the bands at 5.7 μ and the absence of the ν ally at 6.1 μ and 10.1 μ indicate the cyclization to polybenzoxazinedione.

EXAMPLE 9

Relief Structure

A 5 part by weight portion of the soluble prepolymer produced as described in Example 1 and 0.5 parts by weight of maleinanil were dissolved in 10 parts by volume of dimethyl formamide and processed, as described in Example 1, into 4-μ thick films on aluminum plates. The films wre irradiated through a contact mask with a dose of 20 Mrad of electrons and immersed for 30 seconds in a bath of solvent consisting of a mixture of dimethyl formamide/ethanol (1:1), and were subsequently washed with ethanol. Relief structures with sharp edges were obtained. The samples obtained were annealed for 3 hours at 180°C or 15 minutes at 350°C. The edge definition remained unchanged and the relief structures consisted, according to the IR Spectrum (ν imide at 5.6 μ), of the polyimide poly(diphenyloxide pyromellitimide).

What is claimed is:

1. In a method for the preparation of relief structures consisting of highly heat resistant polymers comprising the steps of applying a soluble, photo or radiation-sensitive prepolymer of defined structure in the form of a film to a substrate or in the form of a foil, exposing or irradiating the photo or radiation active layer through a negative pattern, dissolving or stripping of the unexposed or unirradiated portions and annealing the relief structure obtained, the improvement which comprises forming said film or foil from a poly-addition or poly-condensation prepolymer having repeating units of the formula:

wherein, X and D each comprise a carbocyclic and/or heterocyclic nucleus;

G is selected from the group consisting of amide, urea or urethane linkages;

R* is an organic radical containing a photo- or radiation induced di- or polymerizable olefinic double bond; and is a component of ester group CO$_2$R*, said group bound to said nucleus is ortho or peri position to G;

F is a group capable of reacting with the carbonyl group of CO$_2$R* to form a cyclic structure upon heating of the prepolymer to liberate R*OH; and wherein F is arranged in ortho- or periposition to G;

$x$ is 1 or 2; and $y$ is 0 or 2.

2. The method of claim 1 wherein $y$ is 0.

3. The method of claim 1 wherein D is phenylene, pyridinylene, or a radical of the formula wherein M is 0, SO$_2$ or CH$_2$; and $z$ is 0 or 1.

4. The method of claim 1 having repeating units of the formula:

wherein D is as defined in claim 3.

5. The method of claim 4 wherein D is

6. The method of claim 4 wherein D is

7. The method of claim 4 wherein D is

8. The method of claim 4 wherein D is 2,4-pyridinylene.

9. The method of claim 3 wherein the prepolymer has repeating units of the formula:

wherein Q is a hydrogen or CN.

10. The method of claim 3 wherein the prepolymer has repeating units of the formula:

* * * * *

UNITED STATES PATENT AND TRADEMARK OFFICE
CERTIFICATE OF CORRECTION

PATENT NO. : 3 957 512
DATED : May 18, 1976
INVENTOR(S) : Wolfgang Kleeberg et al It is certified that error appears in the above-identified patent and that said Letters Patent are hereby corrected as shown below:

Column 1, line 39, change "resistaant" to --resistant--

Column 5, line 45, change "preferred" to --prepared--

Column 5, line 64, change "carbocyclid" to --carbocyclic--

Column 7, line 23, change "this" to --thus--

Signed and Sealed this

Ninth Day of November 1976

[SEAL]

Attest:

RUTH C. MASON
Attesting Officer

C. MARSHALL DANN
Commissioner of Patents and Trademarks